US005723123A

United States Patent [19]

Karges et al.

[11] Patent Number: 5,723,123
[45] Date of Patent: Mar. 3, 1998

[54] PROCESS FOR THE PRODUCTION OF A VIRUS-FREE CONCENTRATE OF THROMBIN

[75] Inventors: Hermann Karges; Horst Naumann, both of Marburg, Germany

[73] Assignee: Behringwerke Aktiengesellschaft, Marburg, Germany

[21] Appl. No.: 465,191

[22] Filed: Jun. 5, 1995

Related U.S. Application Data

[63] Continuation of Ser. No. 977,842, Nov. 17, 1992, abandoned.

[30] Foreign Application Priority Data

Nov. 19, 1991 [DE] Germany .......................... 41 37 996.9

[51] Int. Cl.$^6$ ............................................. A61K 38/48
[52] U.S. Cl. ........................ 424/94.65; 424/529; 424/530; 530/830; 438/214
[58] Field of Search ........................... 424/94.64, 529, 424/530; 530/830; 435/214

[56] References Cited

U.S. PATENT DOCUMENTS

| | | | |
|---|---|---|---|
| 2,394,566 | 2/1946 | Smith et al. ........................... | 167/78 |
| 4,357,321 | 11/1982 | Thomas ................................ | 424/101 |
| 4,380,511 | 4/1983 | Mannuzza et al. ................... | 424/101 |
| 4,442,655 | 4/1984 | Stroetmann .......................... | 53/428 |
| 4,965,203 | 10/1990 | Silbering et al. .................... | 424/94.64 |
| 5,143,838 | 9/1992 | Kraus et al. .......................... | 435/214 |
| 5,149,540 | 9/1992 | Kunihiro et al. .................... | 424/489 |
| 5,151,355 | 9/1992 | Crowley et al. ..................... | 424/94.64 |
| 5,304,372 | 4/1994 | Michalski et al. ................... | 424/94.64 |
| 5,328,898 | 7/1994 | Greenberg ........................... | 514/12 |
| 5,397,704 | 3/1995 | Boctor et al. ........................ | 435/214 |
| 5,428,014 | 6/1995 | Labroo et al. ....................... | 514/12 |
| 5,506,127 | 4/1996 | Proba et al. .......................... | 435/214 |
| 5,525,498 | 6/1996 | Boctor et al. ........................ | 435/214 |

FOREIGN PATENT DOCUMENTS

| | | |
|---|---|---|
| 0 378 798 A1 | 7/1990 | European Pat. Off. . |
| 0443724 | 8/1991 | European Pat. Off. . |
| 0505604 | 9/1992 | European Pat. Off. . |
| 3229132 A1 | 3/1983 | Germany . |
| 38 09 991 A1 | 10/1988 | Germany . |
| 38 43 126 A1 | 6/1990 | Germany . |
| 4-365481 | 12/1992 | Japan . |

OTHER PUBLICATIONS

Mann, K. G. et al., Multiple Active Forms of Thrombin, The Journal of Biological Chemistry, vol. 246, No. 19, pp. 6106–6114 (Oct. 10, 1971).

Chemical Abstracts, vol. 66: Abstracts No. 83733c, May 8, 1967.

Downing, M.R., et al. "The J. of Biological Chem." vol. 250, #23, Dec. 10, 1975, pp. 8897–8906.

Seegos, W.H., "Proceedings of the Society for Experimental Biology ad Medicine," vol. 72(3), Dec. 1949, pp. 677–680.

Engel, A.M., et al., "The Journal of Biological Chemistry," vol. 246 (5), Mar. 10, 1971, p. 1213–1221.

Guyton, A.C., *"Textbook of Medical Physiology"*—6th ed., 1981, pp. 94–95, Pub. W.B. Saunders Co.

Miale, J. B., *Laboratory Medicine: Hematology*—4th ed., 1972, p. 1063., pub. C.V. Mosby Co.

Becker, C.M.; et al., "Kinetics of the Bio–Conversion of Prothrombin to Thrombin," MIT, Mass., pp. 245–262.

M. Wickerhauser et al., Vox Sang. 22: 137–160 (1972) .

Concise Dictionary of Chemistry, pp. 51 and 264 (1985).

*Primary Examiner*—Chhaya D. Sayala
*Attorney, Agent, or Firm*—Finnegan, Henderson, Farabow, Garrett & Dunner, L.L.P.

[57] ABSTRACT

The invention relates to a process for producing a virus free preparation of thrombin, and the use of said virus free concentrate as a pharmaceutical. For example, the invention relates to a process for the production of a purified and virus free preparation of thrombin which comprises adding a soluble salt in a concentration of from 0.5 mol/l up to the saturation limit thereof, said soluble salt having an anion that forms a sparingly-soluble salt or a soluble complex with calcium, to a solution of a prothrombin complex which has been purified on an anion exchanger and subjected to virus inactivation, said solution having a catalytic amount of thrombin present as a result of the purification, the viral inactivation, or added thereafter at a concentration of greater than zero up to 200 units of thrombin per ml of solution.

16 Claims, No Drawings

PROCESS FOR THE PRODUCTION OF A VIRUS-FREE CONCENTRATE OF THROMBIN

This application is a continuation of application Ser. No. 07/977,842 filed Nov. 17, 1992, now abandoned.

The invention relates to a process which makes it possible to produce a virus-free preparation of thrombin in a simple manner from a pasteurized solution of a prothrombin complex.

Several processes have been described for obtaining thrombin that start from partially-purified prothrombin and then transform this into thrombin by addition of tissue thromboplastin and Ca ions.

Methods are also known for transforming a crude prothrombin concentrate into thrombin using high salt concentrations. This transformation only takes place if all the factors of the prothrombin complex are present in the mixture in sufficient quantity. A prothrombin complex that has been purified on an anion exchanger can be activated with salt if autoprothrombin C (F X) is added. The presence of F VII is also essential.

Because of the danger of transmission of pathogens of viral origin (e.g. hepatitis, AIDS, BSE) with proteins of human or animal origin, procedures for inactivating pathogens are required when producing concentrates containing such proteins.

A number of processes for the production of thrombin are known that contain a step for inactivating pathogens, for example using dry heat.

Processes are also known for inactivating viruses in aqueous solutions of thrombin (DE 38 09 991).

EP 0 378 798, corresponding to DE 38 43 126, describes a process in which the prothrombin complex is bound to an anion exchanger and activated with Ca ions, tissue thromboplastin or activated F X.

All processes that employ tissue thromboplastin for activation of the prothrombin complex have the disadvantage that the former cannot subsequently be removed and represents a source of product contamination.

Activation with high concentrations of salts which complex Ca ions, such as sodium citrate, has the advantage that the prothrombin complex is not additionally contaminated with tissue proteins. However, a prothrombin concentrate that has been purified on DEAE exchangers cannot be activated to thrombin without the addition of activated F X or tissue thromboplastin. It would also be advantageous to carry out virus inactivation even on the prothrombin complex so that the enzyme thrombin, which is labile in comparison with prothrombin, is not exposed to the harsh methods of virus inactivation and does not lose native characteristics as a result of structural changes.

It has now been found, surprisingly, that a prothrombin complex, that has been purified on anion exchangers and pasteurized, can be activated to thrombin by addition of a soluble salt that has an anion that forms a sparingly-soluble salt or a soluble complex with calcium, in a concentration of at least 0.5 mol/l, if the mixture contains a catalytic amount of thrombin (Tab. 1, column b). Without the addition of the salt, the same quantity of thrombin does not activate the prothrombin sufficiently (Tab. 2, column c). Additionally, the activation is temperature-dependent.

The invention therefore relates to a process for producing a purified and virus-free preparation of thrombin, which comprises a soluble salt which has an anion that forms a sparingly-soluble salt or a soluble complex with calcium being added in a concentration of at least 0.5 mol/l to a solution of a prothrombin complex which has been purified on an anion exchanger and subjected to virus inactivation, and a catalytic quantity of thrombin being present in the solution.

A catalytic quantity of thrombin is intended to mean thrombin in a concentration of greater than zero and up to 200, preferably 10 to 50, units per ml.

The catalytic quantity of thrombin can have arisen during the purification process. Otherwise thrombin is added.

The prothrombin complex can have been obtained from animal plasma.

Preferably used is a prothrombin complex that has been purified on DEAE ion exchangers and pasteurized by, for example, the method of EP 0 137 428 at 60° C. for 10 h.

Instead of pasteurization, however, the viruses can also be inactivated in any other suitable way.

Preferably the sulfate, citrate, phosphate or oxalate anion, particularly the citrate anion, is used as calcium-binding anion. The corresponding salt, preferably an alkali metal or ammonium salt, is used at a concentration of from 0.5 mol/l to the particular saturation limit.

Further preferred embodiments comprise using prothrombin complex from animal plasma, or treating with thrombin at 0° C. to 50° C., preferably at 28° C., for 2–100 hours, preferably 5–20 hours.

The process according to the invention allows the production in a simple manner of a native, highly-purified and virus-free concentrate of thrombin that can be used as an hemostatic agent or in a tissue adhesive that is based on fibrinogen and thrombin (fibrin glue).

EXAMPLES

Example 1

16 ml of pasteurized human prothrombin concentrate with 65 U of F II/ml were mixed with 20 U/ml human thrombin and 4 g (25% w/v) of trisodium citrate and incubated at 28° C. once the salt had dissolved. The thrombin activity that was obtained was determined at different times (Table 1b), and at the end of the activation the citrate was removed by dialysis, and the thrombin was lyophilized following stabilization and adjustment to the required activity, e.g., 500 U/ml for use in tissue adhesives such as fibrin glue.

TABLE 1

Activation of prothrombin complex, purified on anion exchangers, with saturated citrate solution as a function of temperature
Thrombin activity (IU/ml) of the mixtures

| Time (h) | a) at 4° C. | b) at 28° C. | c) at 37° C. |
| --- | --- | --- | --- |
| 0 | 15 | 20 | 20 |
| 1 | n.d. | 61 | 63 |
| 3 | 13 | 350 | 1084 |
| 5 | n.d. | 1695 | 3351 |
| 10 | 18 | 5858 | 5141 |
| 21 | n.d. | 8492 | 7393 |
| 25 | 14 | 8978 | 6991 |
| 45 | 94 | 8109 | 7575 |
| 70 | 6800 | n.d.* | n.d. |
| 96 | 7700 | n.d. | n.d. |
| m/u** | 110 | 138 | 117 |

*n.d. = not determined
**m/u = highest thrombin activity obtained per 1 IU of F II

Example 2

18 ml of pasteurized human prothrombin concentrate with 65 U of F II/ml were mixed with 20 U/ml human thrombin and 4.5 g of trisodium citrate and incubated at 37° C. once the salt had dissolved. The thrombin activity that was obtained was determined at different times (Table 1c).

Example 3

8 ml of pasteurized human prothrombin concentrate with 70 U of F II/ml were mixed with 20 U/ml human thrombin/ml and incubated at 37° C. without addition of a salt with calcium-binding anion. The thrombin activities that were obtained after different times are shown in Table 2, column c.

Example 4

10 ml of pasteurized human prothrombin concentrate with 80 U of F II/ml were mixed with 2.5 g of trisodium citrate without addition of thrombin and incubated at 28° C. once the salt had dissolved. Samples were taken after different times and the thrombin activity determined (Table 2, column b).

TABLE 2

Activation of prothrombin complex, purified on anion exchangers, as a function of the species of the prothrombin, of thrombin, and addition of a salt with Ca-binding anion
Thrombin activity (IU/ml) of the mixtures

| Time (h) | a) Bov. prothr., 28° C., citr. | b) Citr., without thrombin, 28° C. | c) Thrombin without addition of salt, 37° C. |
|---|---|---|---|
| 0 | 11 | < 0.1 | 20 |
| 2 | 224 | n.d.* | 36 |
| 4 | 767 | < 0.1 | 52 |
| 6 | 2833 | n.d. | 93 |
| 11 | 4718 | < 0.1 | 222 |
| 25 | 5870 | < 0.1 | 846 |
| 45 | 5921 | < 0.1 | 1090 |
| 70 | n.d. | < 0.1 | 1409 |
| 101 | n.d. | n.d. | 1511 |
| m/u** | 118 | — | 22 |

**n.d. = not determined
**m/u = highest thrombin activity obtained per 1 IU of F II

Example 5

20 ml of pasteurized prothrombin concentrate from bovine plasma with 50 U of F II/ml were mixed with 10 U/ml bovine thrombin and 5 g of trisodium citrate and incubated at 28° C. The thrombin activity that was obtained after different times was determined (Table 2, column a).

Example 6

500 ml of virus-inactivated human prothrombin concentrate with 75 U of F II/ml were mixed with 15 U/ml thrombin and 125 g of trisodium citrate. Once the salt had dissolved at room temperature the solution was incubated at 4° C. Samples were taken after different times and the thrombin activity determined (Table 1, column a).

We claim:

1. A process for the production of a purified and virus free preparation of thrombin which comprises adding a soluble salt in a concentration of from 0.5 mol/l up to the saturation limit thereof, said soluble salt having an anion that forms a sparingly-soluble salt or a soluble complex with calcium, to a solution of a prothrombin complex which has been purified on an anion exchanger and subjected to virus inactivation, said solution having a catalytic amount of thrombin present as a result of the purification of the prothrombin, the viral inactivation of the prothrombin, or added thereafter at a concentration of greater than zero up to 200 units of thrombin per ml of solution.

2. The process as claimed in claim 1 wherein the catalytic amount of thrombin is present in a concentration of 10 to 50 units per ml.

3. The process as claimed in claim 1, wherein the prothrombin complex is from animal plasma.

4. The process as claimed in claim 1, wherein the prothrombin complex is from human plasma.

5. The process as claimed in claim 1, wherein the process takes place at 0° C. to 50° C.

6. The process as claimed in claim 5, wherein the process takes place at 28° C.

7. The process as claimed in claim 1, wherein the prothrombin complex has been purified on DEAE ion exchangers.

8. The process as claimed in claim 1, wherein the anion is sulfate anion, citrate anion, phosphate anion or oxalate anion.

9. The process as claimed in claim 1 wherein the catalytic amount of thrombin is present in a concentration of greater than zero up to 200 units per ml and has been generated during purification of the prothrombin complex.

10. The process as claimed in claim 9, wherein the amount of catalytic thrombin generated during purification of the prothrombin complex is 10 to 50 units per ml.

11. The process as claimed in claim 1 wherein the catalytic amount of thrombin is present in a concentration of greater than zero up to 200 units per ml and has been generated during virus inactivation of the prothrombin complex.

12. The process as claimed in claim 11, wherein the amount of catalytic thrombin generated during virus inactivation of the prothrombin complex is 10 to 50 units per ml.

13. The process as claimed in claim 1 wherein the catalytic amount of thrombin is present in a concentration of greater than zero up to 200 units per ml and has been generated during purification and virus inactivation of the prothrombin complex.

14. The process as claimed in claim 13, wherein the amount of catalytic thrombin generated during purification and virus inactivation of the prothrombin complex is 10 to 50 units per ml.

15. The process as claimed in claim 1, wherein the process is carried out for 2–100 hours.

16. The process as claimed in claim 15, wherein the process is carried out for 5–20 hours.

* * * * *